United States Patent [19]

Janick et al.

[11] 4,204,366
[45] May 27, 1980

[54] METHOD OF NON-AGRICULTURAL PRODUCTION OF COTYLEDONS

[75] Inventors: Jules Janick; Valerie C. Pence, both of West Lafayette, Ind.

[73] Assignee: Purdue Research Foundation, West Lafayette, Ind.

[21] Appl. No.: 951,267

[22] Filed: Oct. 13, 1978

[51] Int. Cl.² .............................................. A01G 1/00
[52] U.S. Cl. ...................................................... 47/58
[58] Field of Search ............................................ 47/58

[56] References Cited

U.S. PATENT DOCUMENTS

| | | | |
|---|---|---|---|
| 2,747,334 | 5/1956 | Routien et al. | 47/58 |
| 3,710,512 | 1/1973 | Tamaki et al. | 47/58 |
| 3,710,805 | 1/1973 | Tamaki et al. | 47/58 X |
| 3,718,153 | 2/1973 | Kobari et al. | 47/58 X |

FOREIGN PATENT DOCUMENTS 1387821  3/1975  United Kingdom ......................... 47/58

OTHER PUBLICATIONS

Fertilization and Embryogeny—Cheesman, Ann. Bot. 41, 1927, pp. 107–126.
Culture in Vitro—Archibald, Nature, Feb. 20, 1954, pp. 351–352.
Initiation & Growth—Hall et al., Ann. Bot., (39), 1975, pp. 555–570.
Hormonal Control—Searles et al, Revista Theobroma, 6(3): 77–81, Jul.—Sep. 1976, Bahia, Brasil.
Growth of Oncobasidium—Prior, Journ. Gen. Microb., 1977–1979, pp. 219–222.
Tissue Culture Studies—Esan, Cocoa Res. Inst. of Nigeria, Ibadan, Nigeria, 1977, pp. 116–125.
Somatic Embryogenesis—Horticultural Reviews, 1979, AVI Publ. Co., Westport, Conn., pp. 1–77.

Primary Examiner—Robert E. Bagwill
Attorney, Agent, or Firm—John R. Nesbitt

[57] ABSTRACT

This invention is a non-agricultural method for producing cotyledons of those plant species whose cotyledons have commercial value for the manufacture of useful products or for direct use as foodstuffs such as *Theobroma cacao* L. (cacao). The method involves three (3) distinct steps, namely, (1) proliferation of cotyledonary embryos by asexual embryogenesis through in vitro culture using a defined media; (2) the growth of the embryo in vitro in a media that will prevent premature germination, and (3) harvest of the in-vitro-grown cotyledon.

8 Claims, No Drawings

METHOD OF NON-AGRICULTURAL PRODUCTION OF COTYLEDONS

FIELD OF THE INVENTION

This invention relates to a method for in vitro production of cotyledons.

BACKGROUND OF THE INVENTION

A research report by Brent H. Tisserat, Edward B. Esan and Toshio Murashige entitled "Asexual Enbryogenesis in Angiosperms" is the most recent and exhaustive report on asexual embryogenesis in vitro known to applicants.

A section of that report states that:

"Table 2 lists the plants, the tissue cultures of which have been reported to generate asexual embryos."

Their Table 2 purports to be a complete survey and does include a few cotyledoneous explants, but there is at least one significant omission, namely cacao, and a further section of the report, entitled "Morphological Aspects of Asexual Embryogeny in Vitro" makes it apparent that the authors have described the current state of the art solely in terms of its agricultural impact, namely the aspect of plant reproducibility, and not in any sense have they related embryogenesis to the use to which it is put by applicants.

The authors thus state their conclusion to be:

"Asexual embryogenesis might be viewed as reflecting a failure of normal development. Nevertheless, it has practical agricultural significance. It enables clonal propagation of some species. The plants derived through asexual embryogeny are often free of many pathogens, especially viruses, that might have infected the original plant (Bitters et al., 1970). Its manifestation in tissue cultures might be used advantageously in clonal multiplication of cultivars that are currently propagated by seeds. We foresee in the very near future clonal seeds from asexual embryos produced in vitro.

The naturally highly polyembryogenic situation has been an obstacle in plant breeding, since it is usually difficult, if not impossible, to distinguish and separate the zygote embryo from the asexual embryos. Methods are needed to enable separation of the two kinds of embryo or to selectively suppress development of the asexual ones."

SUMMARY OF THE INVENTION

The entire history of agriculture and horticulture has been the field or greenhouse growth and cultivation of various plants for their parts, usually fruits and seeds.

With world population and food needs on an inexorable increase, a new method for production of foodstuffs is needed, and is here proposed.

To achieve the present invention it is necessary for the horticulturist or agronomist to divorce himself from the current state of the art described above, and to recognize that in the production of certain commercial crops, for example cacao, what is desired from the commercially grown crop is not the complete cacao tree, nor even the whole cacao bean. What is desired is a massive quantity of the stuff of which the cotyledons of such seeds are largely composed. Once this recognition is made, the techniques of embryogenesis may be put to work. The applicants have proved that, given the right condition, embryogenesis of cacao cotyledons can be obtained.

DETAILED DESCRIPTION OF THE INVENTION

CACAO

*Theobroma cacao*, grown extensively in portions of Africa and South America for the production of cocoa and chocolate, is normally propagated by seed. Typically a small percentage of trees produce the majority of the crop, and thus vegetative propagation of high-yielding clones is desirable. Normal trees can be obtained from cuttings of chupon branches but they are limited in number; cuttings from the numerous fan branches product structurally inferior trees. The traditional agricultural approach suggests propagation through tissue culture might provide a superior alternative to seed or vegetative propagation by cuttings, allowing for rapid production of large numbers of desirable clones. However, cacao regeneration through tissue culture has not yet been reported. Cacao callus has been successfully grown from various tissue, including cambium (Archibald, 1954), seedling root, stem, hypocotyl or cotyledon (Hall and Collin, 1975), leaf and fruit (Searles et al., 1976), embryo and somatic tissue of anthers (Prior, 1977). The development of organized structures from callus has been limited to roots (Hall and Collin, 1975).

This invention does not relate to the potential of cacao for regeneration in tissue culture for the production of superior plants. Nevertheless, the same approaches were used to product the results of this invention that are used by investigators attempting to product new plants.

METHODS AND RESULTS

The basal medium used for in vitro propagation of cacao is as follows:

The murashige and Skoog (1962) salts (M & S Salts) 100 mg/liter inositol, 0.5 mg/liter nicotinic acid, 2.0 mg/liter glycine, 0.1 mg/liter thiamine HCl, 0.5 mg/liter pyrodoxine HCl, 2 g/liter casein hydrolysate, 30 g/liter sucrose, and 10 g/liter agar.

Immature zygotic embryos (2.5 to 10 mm) of Amelonado cacao cultured in the dark on the basal media in the presence of a growth enhancer such as, for example, 1.5 mg/liter naphthaleneacetic acid (NAA) and 100 ml/liter deproteinized coconut water resulted in asexual proliferation of new embryos from the cotyledons on 2 of 10 embryos cultured in the dark and 5 of 8 embryos cultured in the light.

Two distinct types of embryo development were observed both of which occurred in the same cotyledon. In the first type, portions of the cotyledons became swollen and green and folded until embryo axes with cotyledons were formed. In the other type, green swellings appeared, usually at the edge of a cotyledon, and from these swellings new embryos "budded". These buds appeared to progress through the normal developmental stages of the cacao embryo described by Cheesman (1927) to the point at which the embryo appears to be at the same developmental stage as a normal 100–120 day in vivo embryo.

Asexual embryos, when transferred at this stage to liquid basal medium which is free of NAA and coconut water and rotated gently (50 rpm) on a rotary shaker, continue to develop into a mature embryo which were morphologically normal. Fresh weight of these embryos was equivalent to in vivo grown seeds. The cotyledons become thickened and folded, but are not as tightly compressed as those in vivo, as they are not under the constraints of the seed coat.

In an experiment designed to determine the prevalence of asexual embryogenesis 5 genotypes were cultured on the same media and all proliferated embryos. All the 3 cultivars (Amelonado, UF 221, and 41R) with embryos about 2-4 mm long (100-120 day stage) proliferated in at least 80% of the cotyledons in 3 weeks; proliferation in SIAL 93 and UF 11 where embryos were larger (10-15 mm) had proliferation frequencies of 47% and 38%, respectively.

CONCLUSION

These experiments demonstrate that immature sexual embryos of *T. cacao* proliferate asexual embryos in the basal media described containing conconut water and NAA, and grow. Embryogenesis of cacao or soybean has never been observed in various studies of our own and of others using any other tissue.

Cacao is a crop grown specifically for the cotyledon. The product of commerce in cacao is obtained when mature seeds are removed from the pods, fermented, and dried. These are then shipped to the consuming nations, where they are roasted to produce cocoa and chocolate.

The present invention teaches a system in which cacao cotyledons are produced in large numbers in vitro.

This invention teaches a method whereby cacao is produced in vitro under controlled conditions.

What is claimed is:

1. A non-agricultural method for production of cotyledons comprising the steps of:
   (A) Proliferation of immature cotyledonary zygotic cocoa embryos in a basal media in the presence of a growth enhancer whereby asexual embryos are initiated upon said zygotic embryos; and
   (B) Growing said embryos in vitro in a basal medium; and
   (C) Harvesting the cotyledons so produced.

2. The method according to claim 1 in which the embryo is of the species Theobroma cacao L.

3. The method according to claim 1 in which the basal media is comprised of M and S salts, 100 mg/liter inositol, 0.5 mg/liter nicotinic acid, 2.0 mg/liter glycine, 0.1 mg/liter thiamine HCl, 0.5 mg/liter pyridoxine HCl, 2 g/liter casein hydrolysate, 30 g/liter sucrose, and 10 g/liter agar.

4. The method according to claim 1 in which said embryos are grown in the light.

5. The method according to claim 1 in which said embryos are grown in the dark.

6. The method according to claim 1 in which the growth takes place at normal ambient temperatures.

7. The method according to claim 1 in which said growth enhancer is comprised of a mixture of naphthaleneacetic acid and deproteinized coconut water.

8. The method according to claim 7 in which said growth enhancer is comprised of a solution of about 1.5 mg/liter naphthaleneacetic acid and about 100 ml/liter of deproteinized coconut water.

* * * * *